(12) United States Patent
Kettel et al.

(10) Patent No.: US 11,065,361 B2
(45) Date of Patent: Jul. 20, 2021

(54) WATER-CONTAINING HYDROGELS FOR DRESSING WOUNDS

(71) Applicant: PAUL HARTMANN AG, Heidenheim (DE)

(72) Inventors: Markus Kettel, Heidenheim an der Brenz (DE); Hanno Richter, Möhrendorf (DE)

(73) Assignee: Paul Hartmann AG, Heidenheim (DE)

( * ) Notice: Subject to any disclaimer, the term of this patent is extended or adjusted under 35 U.S.C. 154(b) by 253 days.

(21) Appl. No.: 16/471,245

(22) PCT Filed: Dec. 21, 2017

(86) PCT No.: PCT/EP2017/084043
§ 371 (c)(1),
(2) Date: Jun. 19, 2019

(87) PCT Pub. No.: WO2018/115257
PCT Pub. Date: Jun. 28, 2018

(65) Prior Publication Data
US 2021/0128779 A1    May 6, 2021

(30) Foreign Application Priority Data
Dec. 23, 2016    (DE) .......................... 102016125534.3

(51) Int. Cl.
*A61F 13/02* (2006.01)
*A61L 26/00* (2006.01)
(Continued)

(52) U.S. Cl.
CPC ........ *A61L 26/008* (2013.01); *A61F 13/0206* (2013.01); *A61F 13/0213* (2013.01);
(Continued)

(58) Field of Classification Search
CPC .......... A61L 15/28; A61L 15/60; A61L 15/44; A61L 15/18; A61L 31/06; A61L 2300/252; A61L 2300/254; A61L 2300/608; A61L 24/043; A61L 24/104; A61L 26/0004; A61L 26/0009; A61L 26/0047;
(Continued)

(56) References Cited

U.S. PATENT DOCUMENTS 5,051,661 A    9/1991 Lee
5,059,424 A    10/1991 Cartmell et al.
(Continued)

FOREIGN PATENT DOCUMENTS

DE    68727278 T2    4/1997
EP    0426422 A2    5/1991
(Continued)

OTHER PUBLICATIONS

International Search Report and Written Opinion from PCT/EP2017/084043 dated Apr. 11, 2018.
(Continued)

*Primary Examiner* — Ophelia A Hawthorne
(74) *Attorney, Agent, or Firm* — Dilworth & Barrese, LLP

(57) ABSTRACT

The invention relates to water-containing hydrogels for dressing wounds, comprising a polyurethane-polyurea copolymer having a polyvalent alcohol, except propylene glycol.

18 Claims, 3 Drawing Sheets

(51) Int. Cl.
*A61L 15/22* (2006.01)
*A61L 15/60* (2006.01)

(52) U.S. Cl.
CPC ............ *A61L 15/225* (2013.01); *A61L 15/60* (2013.01); *A61L 26/0052* (2013.01)

(58) Field of Classification Search
CPC ...... A61L 31/16; A61L 26/008; A61L 15/225; A61L 26/0052; A61L 15/26; A61L 26/0066; A61L 2300/412; A61L 26/0057; A61F 13/0206; A61F 13/0213; A61F 13/00; A61F 13/02; A61F 13/0243; A61F 13/0246; A61F 13/534; A61K 9/0014; A61K 47/12; A61K 9/00
See application file for complete search history.

(56) References Cited

U.S. PATENT DOCUMENTS

| | | | |
|---|---|---|---|
| 8,753,669 | B2 | 6/2014 | Cleary et al. |
| 9,579,413 | B2 | 2/2017 | Junginger et al. |
| 10,130,521 | B2 | 11/2018 | Junginger et al. |
| 2013/0060216 | A1 | 3/2013 | Junginger et al. |

FOREIGN PATENT DOCUMENTS

| | | | |
|---|---|---|---|
| EP | 0630629 | A1 | 12/1994 |
| EP | 2338528 | A1 | 6/2011 |
| EP | 2338529 | A1 | 6/2011 |
| EP | 2767293 | A1 * | 8/2014 ......... A61L 26/0057 |
| EP | 2767293 | A1 | 8/2014 |
| RU | 2053795 | C1 | 2/1996 |
| RU | 2286801 | C2 | 11/2006 |
| RU | 73198 | U1 | 5/2008 |
| RU | 2422133 | C1 | 6/2011 |
| RU | 2424825 | C2 | 7/2011 |
| RU | 2519683 | C2 | 6/2014 |
| RU | 2526175 | C2 | 8/2014 |
| WO | 2010000450 | A2 | 1/2010 |
| WO | 20100000451 | A1 | 1/2010 |
| WO | 2011095194 | A1 | 8/2011 |
| WO | 2014127983 | A1 | 8/2014 |

OTHER PUBLICATIONS

Huntsman Corporation : The Jeffamine® Polyetheramines—Produktübersicht von 2007 zum Download: URL: www.huntsman.com, [abgerufen am Aug. 28, 2017].

Carpenter: Aquapol PL-13000-31—material safety data sheet URL: http://carpenter.com/docs/chemical-systems/AQUAPOL%20PL-13000-31.pdf. [abgerufen am Aug. 28, 2017].

Russian Office Action from PCT/EP2017/084043 dated Dec. 4, 2020.

* cited by examiner

WATER-CONTAINING HYDROGELS FOR DRESSING WOUNDS

This application claims priority to German Patent Application No. 102016125534.3 filed on Dec. 23, 2016 the entire contents of which are incorporated herein in their entirety.

The present invention concerns aqueous hydrogels for the treatment of wounds.

The healing of skin wounds is based on the ability of the skin to regenerate epithelium and also connective and supporting tissue. The regeneration itself is characterized by a complex event of overlapping cellular activities which advance the healing process step by step. Three essential healing phases of a wound, especially in the case of wounds with loss of tissue, are thus described in the literature. These include the inflammatory or exudative phase for hemostasis and wound cleansing (phase 1, cleansing phase), the proliferative phase for construction of granulation tissue (phase 2, granulation phase) and the differentiation phase for epithelialization and scarring (phase 3, epithelialization phase). It has become apparent that wound healing is particularly assisted by a moist wound treatment. As part of a wound treatment, it is possible to use, inter alia, wound dressings composed of various materials.

It is known that disturbances may occur during wound healing. In the event of a disturbed wound healing, necroses and pathological microorganisms may have an adverse effect on physiological metabolism while wound healing takes place. In many cases, this may lead to local hypoxia, the possible result thereof being then a further degradation of the surrounding tissue. This degradation of the surrounding tissue may, in turn, additionally hamper wound healing, with the possibility of chronic wounds occurring. In the context of this invention, chronic wounds refer to wounds which do not heal within an expected period of from 4 to 6 weeks.

Furthermore, scars may remain when wounds are not optimally treated. At best, the scars impair the affected tissue only cosmetically, but not in terms of how it functions. Otherwise, it is, however, also possible for the scarred tissue to lose functional properties, such as its elasticity and sensitivity.

What escapes from wounds is an exudate which has a complex composition. Said exudate contains not only growth-promoting substances, but also substances that complicate tissue construction, the opposing effects of which have a critical influence on the course of wound healing.

Aqueous hydrogels are used with success as a constituent of wound dressings in the moist treatment of wounds. They are capable of taking up wound exudate, which escapes from the wound, into the gel matrix and of releasing moisture from the gel matrix, meaning that the wound is provided with a wound healing-promoting environment. In many cases, they are the wound contact layers of wound dressings. While the wound dressings rest on the wound to be treated, the absorption capacity and the moisture-release capacity are exhausted over time, meaning that the wound dressings containing an aqueous hydrogel must be changed repeatedly until the wound is completely healed. In this connection, a dressing change is a critical situation for the patient, because what may be carried away with the dressing are dressing-adhering constituents of the wound tissue or of the sensitive skin surrounding the wound. In order to be able to minimize the trauma of the dressing change, special requirements are placed on the wound contact layer. For instance, the capacity of the hydrogel for adhesion to wound tissue and/or skin must not be too great, even though an initial adhesion of the hydrogel when applying the wound dressing is definitely desired for better fixability.

Furthermore, to maintain a wound healing-promoting environment, it is desirable to provide a cell-compatible hydrogel composition. What is advantageous is a composition which is capable of binding harmful factors of the wound exudate and of thus removing them from the wound tissue, and of concentrating wound healing-promoting components of the wound exudate and of thus providing the wound tissue therewith in a higher concentration.

Lastly, wound dressings should be comfortable to wear for the patient and should limit the freedom of movement of the affected body parts as little as possible so as not to adversely affect the patient's therapy compliance.

EP630629 discloses aqueous hydrogel matrices comprising a polyurethane-polyurea copolymer and propylene glycol for wound treatment.

WO2010/000450 and WO2010/000451 disclose foam-containing wound dressings having an aqueous hydrogel matrix comprising a polyurethane-polyurea copolymer.

EP2338528 and EP2338529 disclose aqueous hydrogel matrices comprising a polyurea-polyurethane copolymer and propylene glycol having improved absorption and adhesion properties.

However, it has emerged that both wound healing in the above method is still improvable. In particular, the constituent propylene glycol was identified as disadvantageous. In addition, the known wound dressings may lead to skin irritations and are still optimizable with respect to the patients' therapy compliance.

There is continuous interest in providing means which meet the stated requirements better. The subject matter of claim 1 achieves this object.

The goal of the present invention is to overcome the disadvantages from the prior art.

In particular, the object is to provide for the use of substances in the treatment of wounds, which substances lead to an improved wound healing. The substances, or the wound care products containing said substances, should be felt by the patient to be comfortable, have a good compatibility for wound tissue and skin and lead to an advantageous therapy compliance.

It is therefore an object of the present invention to provide an improved wound care product which influences the pathological state of a wound such that a rapid course of wound healing can take place. Said wound care product is to be attached as needed in all wound healing phases in order to ensure the above-mentioned effect.

In the context of this invention, a wound usually exists when tissue coherence has been interrupted on an external or internal body surface.

There are different types of wounds. For instance, a wound which heals by primary intention is understood to mean a wound having non-gaping wound edges, which is distinguished by healing without complications and without infection. These wounds frequently occur in body parts having a good blood supply. The wound edges which are non-gaping and are thus close to one another may, for example, have been caused by a (surgical) cut. If no further treatment takes place, the wound closes without complications.

Further wounds are wounds which heal by secondary intention. A wound which heals by secondary intention is understood to mean a wound when a) there is a loss of tissue and/or b) microbial contamination has occurred, which prevents healing by primary intention. The organism can compensate for the loss of tissue via tissue to be regenerated and epidermization. This leads, in the context of wound healing by secondary intention, via the formation of a granulation tissue until the tissue gap is replaced with a scar.

In a preferred embodiment of the present invention, the wound which heals by secondary intention is a mechanical wound, a thermal wound, or a wound caused by chemical substances or by radiation.

Mechanical wounds may arise as a result of the external action of force. These include, for example, cuts, stab wounds, lacerations, contusions, abrasions, scratches, bites and bullet wounds.

Thermal wounds are essentially caused by intense heat or cold exposure. These include, for example, burns, scalds, frostbites and also injuries caused by electric current.

Chemical wounds are understood to mean chemical burns. These can, for example, be caused by acidic, alkaline, oxidizing and/or reducing substances.

Wounds caused by radiation are also referred to as actinic wounds. These are, for example, triggered by ionizing radiation and may have an appearance similar to that of burns.

Chronic wounds may be defined as wounds, the course of healing of which differs from normal wound healing in one stage or all stages of wound healing. Thus, acute, normal-healing wounds may give rise, for example as a result of a wound infection, to a chronic wound, which is characterized by a delayed speed of healing. In this connection, the transition from an acute wound to a chronic wound may take place in any stage of wound healing. Chronic wounds are clinically defined as wounds, the healing of which requires more than 6-8 weeks, this definition not correctly covering all clinical pictures. Chronic wounds are more a diagnosis which is based on the clinical experience of medical personnel.

In particular, chronic wounds arise because of mechanical load (decubitus ulcer, pressure ulcers, pressure sore), venous insufficiency (ulcus cruris venosum, venous ulcers), arteriosclerosis (ulcus cruris arteriosum, arterial ulcers), neuropathic changes (diabetic foot, neuropathic ulcers), but also as a consequence of autoimmune disease, of tumors (ulcerating tumors) or radiation damage in the case of tumor therapy.

Decubitus ulcers are defined as a trophic disturbance of tissues (especially skin and subcutaneous tissue) that is caused by external (relatively long-term) action of pressure with compression of vessels and local ischemia, accompanied by necroses, maceration and possibly infection. Decubitus ulcers arise especially in the case of bed confinement, in particular at sites of the body at which the skin lies directly against the bone, but also, for example, under poorly fitting protheses and excessively tight plaster casts.

Decubitus ulcers are divided into the following stages. Here, stage II, stage III and stage IV decubitus ulcers in particular are known as chronic wounds:

Decubitus ulcer—stage I: This concerns a persistent, circumscribed erythema which remains even when pressure is relieved. The redness has a sharp border and may harden or be hyperthermic. The skin is still intact.

Decubitus ulcer—stage II: Blistering and skin abrasion and, as a result, partial skin loss occur in this phase. The epidermis right up to parts of the dermis is damaged. In this phase, there is a superficial wound or flat sore.

Decubitus ulcer—stage III: In this advanced stage, it is already possible to observe a loss of all skin layers. Furthermore, it is possible to observe damage to the subcutaneous tissue and, possibly, necroses, which may reach up to the underlying muscle tissue. From experience, a delimitation of the necrotic tissue must first occur before the entire extent of the tissue damage is discernible. Decubitus ulcer III appears clinically as an open, deep sore.

Decubitus ulcer—stage IV: In this extremely critical stage, it is possible to register a loss of all skin layers with extensive destruction, tissue-necrosis or damage of muscles, bones or supporting structures (tendons, joint capsules). Decubitus ulcer IV appears clinically as an open and deep sore of large surface area.

The inflammatory phase usually occurs directly after the trauma and lasts approximately three days. It is characterized by vessel contraction, activation of the coagulation cascade and complex immunological processes. What generally occurs is the formation of a fibrin mesh, which closes the wound and protects it externally. The release of vasoactive substances (e.g., histamine and serotonin) can cause a local inflammatory reaction. The surrounding vessels can dilate and, as a result of an increased capillary permeability, leukocytes can migrate to the site of inflammation. They can eliminate microorganisms and tissue necroses. The wound can be cleansed as a result.

The subsequent proliferation or granulation phase usually starts about on the second day after wound formation and can, for example, last up to 14 days. What occurs is the construction of new tissue with vascular sprouting and defect filling by granulation tissue. This is the basic prerequisite for later epithelialization. Fibroblasts from the surrounding tissue can migrate into the fibrin mesh and use it as a provisional matrix. The construction of collagen fibers begins. Via the enzyme plasmin, the fibrin scaffold can be degraded by means of fibrinolysis. The closed vessels can be recanalized.

The maturation of the collagen fibers usually starts with the differentiation or remodeling phase, about between the sixth and tenth day. The wound contracts owing to the conversion of fibroblasts into fibrocytes and myofibroblasts. As a result, the scar tissue shrinks and it leads to a reduction in the size of the wound. Epithelialization from the wound edge brings wound healing to an end.

In a preferred embodiment of the present invention, the treatment of the wounds, preferably of the wounds which heal by secondary intention, is a phase-appropriate wound treatment. In the context of this application, a phase-appropriate wound therapy is understood to mean that the wound therapy is responsive to the specific needs of the wound in the individual phases.

Thus, the phase-appropriate treatment can be effected in a targeted manner in one or more phases of wound healing. (In contrast, the same treatment is effected across all phases in the case of conventional wound treatments).

In the context of the invention, the term hydrogel refers to a finely dispersed system composed of at least one solid phase and one liquid phase. Said solid phase forms a spongy, three-dimensional network, the pores of which are filled by a liquid (lyogel) or else a gas (xerogel). Preferably, there is complete interpenetration of both phases. As a result of water uptake, the three-dimensional network can increase its volume owing to swelling, without losing structural cohesion at the same time. Preferably, a hydrogel can be constructed from a synthetic or natural material, preferably from a hydrophilic synthetic material.

Hereinbelow, the term hydrogel is also referred to synonymously as hydrogel composition or hydrogel matrix.

The present invention has, as solid phase, a polymer containing polyurethane and polyurea groups. The liquid phase used is a mixture of water and polyhydric alcohol, except propylene glycol.

Hereinbelow, percentages relating to the concentration of ingredients are understood to mean that they refer to the proportion of the stated staring materials in the total reaction mixture composed of prepolymers, water, polyhydric alcohol and optionally salt.

In connection with the present invention, the aqueous hydrogels used can be in particular hydrogels which form a coherent, discrete layer and do not release water under a pressure which occurs when the hydrogel is used as intended.

The present invention provides aqueous hydrogels for the treatment of wounds obtainable by reacting an a) amine-terminated prepolymer containing polyalkylene oxide units with an b) isocyanate-terminated prepolymer containing polyalkylene oxide units, the reaction taking place in the presence of a polyhydric alcohol, except propylene glycol, and in the presence of water and, based on the total mass of all reactants, the sum total of the masses of amine-terminated prepolymer and isocyanate-terminated prepolymer being 10-30% by weight of the total mass of all reactants and the mass of the polyhydric alcohol, except propylene glycol, being 5-35% by weight of the total mass of all reactants and the mass of the water used being at least 40% by weight of the total mass of all reactants, the molar ratio of reactive isocyanate end groups to reactive amine end groups being 1.0 to 2.0, preferably 1.0 to 1.8, particularly preferably 1.0 to 1.6, very particularly preferably 1.0 to 1.5 and most preferably 1.2 to 1.3.

In a preferred embodiment, the invention provides an aqueous hydrogel for the treatment of wounds obtainable by reacting an a) amine-terminated prepolymer containing polyalkylene oxide units with an b) isocyanate-terminated prepolymer containing polyalkylene oxide units, the reaction taking place in the presence of a polyhydric alcohol, except propylene glycol, and in the presence of water and, based on the total mass of all reactants, the sum total of the masses of amine-terminated prepolymer and isocyanate-terminated prepolymer being 15-25% by weight of the total mass of all reactants and the mass of the polyhydric alcohol, except propylene glycol, being 5-35% by weight of the total mass of all reactants and the mass of the water used being at least 40% by weight of the total mass of all reactants, the molar ratio of reactive isocyanate end groups to reactive amine end groups being 1.0 to 2.0, preferably 1.0 to 1.8, particularly preferably 1.0 to 1.6, very particularly preferably 1.0 to 1.5 and most preferably 1.2 to 1.3.

In particular, the hydrogel is, in this connection, obtainable by reacting an amine-terminated prepolymer containing polyethylene oxide units and/or polypropylene oxide units with an at least three-armedly branched isocyanate-terminated prepolymer containing polyethylene oxide units and/or polypropylene oxide units in the presence of a polyhydric alcohol, except propylene glycol, the molar ratio of reactive isocyanate end groups to reactive amine end groups being 1.0 to 2.0, preferably 1.0 to 1.8, particularly preferably 1.0 to 1.6, very particularly preferably 1.0 to 1.5 and most preferably 1.2 to 1.3.

In particular, the hydrogel is, in this connection, obtainable by reacting an amine-terminated prepolymer containing polyethylene oxide units and polypropylene oxide units with an at least three-armedly branched isocyanate-terminated prepolymer containing polyethylene oxide units and polypropylene oxide units in the presence of a polyhydric alcohol, except propylene glycol, the ratio of reactive isocyanate end groups to reactive amine end groups being 1.0 to 2.0, preferably 1.0 to 1.8, particularly preferably 1.0 to 1.6, very particularly preferably 1.0 to 1.5 and most preferably 1.2 to 1.3 and the weight ratio of polyethylene oxide units to polypropylene oxide units both in the amine-terminated prepolymer and in the isocyanate-terminated prepolymer being 3:1 to 7:1.

A typical amine-terminated prepolymer is, for example, a triblock polymer composed of propylene glycol, ethylene glycol and again propylene glycol units, the polymer being amine-functionalized at each end with 2-aminopropyl groups. It has a content of reactive amine end groups of 0.9554 mmol/g at a molecular weight of on average about 2000 g/mol and a dispersity of 1.08, measured by gel permeation chromatography, and a molar ratio of ethylene units to propylene units of 3:1 to 7:1, preferably 39:6. Such an amine-terminated prepolymer is, for example, commercially available as Jeffamin® ED-2003, Huntsman; Everberg, Belgium.

A typical isocyanate-terminated prepolymer having aliphatic diisocyanate groups is, for example, a three-armed copolymer composed of propylene glycol units and polyethylene glycol units, which has been reacted at each end with one molecule of isophorone diisocyanate. It has a content of reactive isocyanate end groups (NCO groups) of 3.0% to 3.4%, preferably 3.2%, and a molar ratio of ethylene oxide units to propylene oxide units of 3:1 to 4:1. Such an isocyanate-terminated prepolymer having aliphatic diisocyanate groups is, for example, commercially available as Aquapol® PL-13000-3 (Carpenter; Richmond, USA).

Particular preference is given to a hydrogel obtainable by reacting said amine-terminated prepolymer Jeffamin® ED-2003 with said isocyanate-terminated Aquapol® PL-13000-3 in the presence of a polyhydric alcohol, except propylene glycol, the mass ratio of Aquapol to Jeffamin being between 1.0 and 2.5, preferably between 1.1 and 1.7. These gels exhibit sufficient gel strength for use in wound dressings, whereas, when the ratio is lower, the products obtained are viscous liquids and, when the ratio is higher, the products obtained are rigid gel bodies.

These hydrogels are particularly well suited to storing water and to releasing said water to a wound.

In the case of the stated hydrogels, the solid phase is not solely formed by a polymer arising from the reaction between an amine-terminated prepolymer and an isocyanate-terminated prepolymer. Also involved in the reaction is a polyhydric alcohol, except propylene glycol, the free hydroxyl groups of which can react with isocyanate groups. The polyhydric alcohol component contributes, in this connection, to an additional crosslinking, which, especially in the case of polyhydric alcohols having more than two hydroxyl groups, leads to a three-dimensional crosslinking of the prepolymers. The reaction between a polyhydric alcohol and an isocyanate group gives rise to a carbamic ester, which is also referred to as urethane. This reaction can be quickened by acids or bases as catalyst and be reversed by supply of thermal energy. If the reaction temperature is held constant between 5° C. and 30° C., preferably between 5° C. and 20° C., said reaction can be effected in a sufficient ratio, with the result that hydrogels having covalently incorporated polyhydric alcohols are obtained, which have advantageous properties.

Further preferably, hydrogels according to the invention contain at least one polyhydric alcohol from the group of comprise dihydric, trihydric, tetrahydric, pentahydric or hexahydric alcohols. In particular, the alcohol can be selected from the group of glycols, especially ethylene glycol, polyethylene glycols having a mass of from 200 g/mol to 6000 g/mol, preferably polyethylene glycols having a mass of from 300 g/mol to 2000 g/mol, and also sorbitol or glycerol or mixtures thereof. These alcohols are outstandingly suitable as moisturizer and thus represent a care component for the skin surrounding the wound.

Hydrogels containing one or more of these alcohols as partner in the above-described reactions exhibit a high absorption capacity for wound exudate and a reduced moisture loss. They exhibit an adhesive force which allows an atraumatic dressing change. Because of their low cytotoxicity, they are very highly compatible for wound tissue. In addition, such gels are capable of concentrating growth factors of the wound exudate that are necessary for wound healing and of thus quickening wound healing. This is particularly true for glycerol-containing hydrogels.

In a preferred embodiment, the polyhydric alcohol used is glycerol, especially in a concentration of 10-25% by weight. Such hydrogels exhibit particularly advantageous properties with respect to cell compatibility, liquid loss and adhesion capacity.

In a particularly preferred embodiment, the polyhydric alcohol used is glycerol in a concentration of 15-25% by weight. Such hydrogels also exhibit a particularly high absorption capacity.

In a further preferred embodiment, the polyhydric alcohol used is ethylene glycol in a concentration of 5-30% by weight, preferably 10-25% by weight and particularly preferably 15-20% by weight. Such hydrogels exhibit advantageous properties with respect to moisture loss, absorption capacity and cell compatibility.

In a further preferred embodiment, the polyhydric alcohol used is sorbitol in a concentration of 5-30% by weight, preferably 10-25% by weight and particularly preferably 15-20% by weight. Such hydrogels exhibit advantageous properties with respect to absorption capacity and cell compatibility.

In a further preferred embodiment, the polyhydric alcohol used is PEG300 in a concentration of 5-30% by weight, preferably 10-25% by weight and particularly preferably 15-20% by weight. Such hydrogels exhibit advantageous properties with respect to moisture loss and absorption capacity.

In a further preferred embodiment, the polyhydric alcohol used is PEG2000 in a concentration of 5-30% by weight, preferably 10-25% by weight and particularly preferably 15-20% by weight. Such hydrogels exhibit advantageous properties with respect to cell compatibility.

A further group of polyhydric alcohols is formed by mono-, di-, oligo- and polysaccharides and also the corresponding sugar alcohols thereof. Suitable monosaccharides are, in this connection, glyceraldehyde, dihydroxyacetone, erythrose, threose, erythrulose, ribose, arabinose, xylose, lyxose, deoxyribose, ribulose, xylulose, allose, altrose, glucose, mannose, gulose, idose, galactose, talose and fructose. A preferred monosaccharide is glucose. Disaccharides are substances which formally arise from two units of the stated monosaccharides by elimination of water. Suitable disaccharides are cellobiose, gentiobiose, isomaltose, isomaltulose, lactose, lactulose, laminaribiose, maltose, maltulose, melibiose, neohesperidose, neotrehalose, nigerose, rutinose, sambubiose, sophorose, sucrose and trehalose.

In a further preferred embodiment, the polyhydric alcohol used is sucrose in a concentration of 5-30% by weight, preferably 10-25% by weight and particularly preferably 15-20% by weight. Such hydrogels exhibit advantageous properties with respect to moisture loss, absorption capacity and cell compatibility.

Oligosaccharides formally consist of three to ten units of the stated monosaccharides, which are connected to one another with elimination in each case of one water molecule. Polysaccharides formally consist of more than ten units of the stated monosaccharides, which are connected to one another with elimination in each case of one water molecule. Suitable polysaccharides are cellulose, glycogen, amylose, amylopectin, pectins, chitin, callose, chitosan and sodium carboxymethylcellulose.

A hydrogel according to the invention contains at least 40% by weight and very particularly preferably at least 50% by weight of water, the hydrogel comprising further preferably not more than 90% by weight and further preferably not more than 80% by weight of water. Thus, it is possible to provide a hydrogel for wound treatment that provides an amount of moisture that is sufficient for natural wound healing.

Furthermore, the aqueous hydrogel matrix can comprise in particular at least one salt. In particular, the hydrogel matrix comprises here an inorganic salt. In this connection, what are particularly suitable are chlorides, iodides, sulfates, hydrogensulfates, carbonates, hydrogencarbonates, phosphates, dihydrogenphosphates or hydrogenphosphates of the alkali metals and alkaline earth metals. Preferably, the hydrogel matrix comprises sodium chloride, potassium chloride, magnesium chloride, calcium chloride or mixtures thereof. Particular preference is given to sodium chloride. These salts simulate particularly well the electrolyte mixture in a wound serum released by a wound. This means that a hydrogel matrix comprising these salts provides a wound with conditions which particularly promote wound healing.

Here, the hydrogel matrix can comprise 0% to 5% by weight of at least one salt. In particular, the hydrogel matrix comprises 0.1% to 3% by weight of a salt and very particularly preferably 0.5% to 1.5% by weight of a salt.

Hydrogels according to the invention are suitable for the treatment of wounds. They can be distributed onto a wound surface as semi-solid, plastically deformable masses by means of suitable applicators. In this connection, suitable applicators are, for example, tubes or adapted syringes.

Hydrogels according to the invention are preferably a constituent of a wound dressing. In the context of the present invention, a wound dressing is understood to mean a product which is applied to a wound is provided in a ready-to-use form. Suitable wound dressings have, in this connection, at least one layer composed of a support material and one layer comprising a hydrogel according to the invention.

The support layer used can be in particular polymer films or polymer foams, preferably films or foams made from polyurethane, polyether urethane, polyester urethane, polyether-polyamide copolymers, polyacrylate or polymethacrylate. In particular, a water-impermeable and water vapor-permeable polyurethane film or a water-impermeable and water vapor-permeable polyurethane foam is suitable as support layer. In particular, a polyurethane film, polyester urethane film or polyether urethane film is preferred as polymer film. However, what are also very particularly preferred are those polymer films which have a thickness of from 15 µm to 50 µm, especially 20 µm to 40 µm and vary particularly preferably from 25 µm to 30 µm. The water vapor-permeability of the polymer film of the wound dressing comprises preferably at least 750 g/m$^2$/24 h, especially at least 1000 g/m$^2$/24 h and very particularly preferably at least 2000 g/m$^2$/24 h (measured in accordance with DIN EN 13726). In particularly preferred embodiments, said films comprise a moisture-tight, adhesive edge section. Said edge section ensures that the wound system can be applied and fixed at its intended site. Furthermore, it is ensured that no liquid can escape between the film and the skin surrounding the area to be treated. What are considered to be particularly preferred are those adhesives which exhibit, in a thin application of 20 g/m² to 35 g/m² together with the film, a water vapor-permeability of at least 800 g/m²/24 h and preferably of at least 1000 g/m²/24 h (measured in accordance with DIN EN 13726).

In a preferred embodiment, the absorbent layer comprises a hydrophilic polyurethane foam and the hydrogel. For example, the surface of a hydrophilic polyurethane foam can be impregnated or coated with the hydrogel or be completely or partially permeated by said gel.

In an alternative embodiment, the hydrogel composition can also be present adjacent to or spatially separated from the absorbent layer. For example, the hydrogel composition, for example comprising a polyurethane-polyurea copolymer, can be coated onto a surface of a layer composed of a polyurethane foam, with the result that a hydrogel layer comprising the hydrogel composition rests in direct contact on a layer composed of polyurethane foam. Alternatively, the hydrogel layer and the absorbent layer can also be separated from one another by a spacer layer. For example, the spacer layer can comprise a hydrogel matrix, a polymer film, a hydrocolloid matrix, a polymer mesh, a textile fabric, an adhesive and/or a polymer mesh.

Furthermore, the multilayer wound dressing can also comprise further layers besides the absorbent layer and the support layer, such as, for example, a wound contact layer, one or more barrier layers and/or one or more distributor layers.

Preferred wound dressings comprise a support layer, a hydrogel layer according to the present invention and optionally an absorbent layer arranged between the hydrogel layer and the support layer. The absorbent layer can preferably comprise a fibrous material, particularly preferably a hydrophilic polyurethane foam. The hydrogel layer can be continuous or discontinuous. For example, it can be applied over the entire surface of the support layer or comprise channels, holes or differently shaped openings. In the case of a discontinuous hydrogel layer, it is possible to apply on the support layer and/or on the absorbent layer a multiplicity of discrete hydrogel elements, which can have the shape of circles, squares or other regular or irregular polygons.

Possible arrangements of the various layers in multilayer wound dressings according to the invention are, for example, described in WO 2010/000450, to which reference is hereby made in full.

The wound dressings further exhibit a high level of comfort for the patient, by being easy-to-use, skin-friendly, soft, thin, skin-fitting and analgesic (via a hydrogel cooling effect), and can thus be used even over a long period, usually 3 to 5 days, before the wound dressing is changed. The support material can be coated with an adhesive in a continuous or discontinuous manner over the entire surface or partially.

In a wound dressing according to the invention, a hydrogel according to the invention can be directly applied on a support layer. It can also be applied with the aid of an adhesive for better cohesion. Further layers can be arranged between the support layer and the hydrogel layer. It has been found to be advantageous when a wound dressing comprises, as additional layer, a layer which is capable of taking up liquid, of storing it and/or of distributing it within the layer or transferring it to further layers. Suitable layers which are capable of taking up liquids are nonwoven materials composed of natural or synthetic fibers or mixtures thereof, open-pore foam materials or materials containing a hydrophobic matrix containing liquid-uptake particles. Preference is given to an open-pore foam material composed of polyurethane. A wound care product according to the invention preferably comprises a hydrophilic polyurethane foam. The use of a hydrophilic polyurethane foam is advantageous for a rapid wound healing, because such foams exhibit a high absorption capacity and are therefore preferably used in the cleansing phase of wound healing with strong exudation. A further advantage of polyurethane foams is that only low shear forces are exerted on a wound to be treated and the wound is thus well padded.

In connection with the present invention, a hydrophilic polyurethane foam is understood to mean a polyurethane foam which can take up and store thus absorb a liquid in its polyurethane matrix and in its pores and can release at least some of the liquid taken up. What are suitable here as hydrophilic polymer foams are, in particular, open-pore, hydrophilic polyurethane foams. Accordingly, a particularly preferred wound dressing comprises a layer comprising an open-pore, hydrophilic polyurethane foam. According to the invention, what are to be preferably used are polyurethane foams which exhibit a high absorption capacity for liquids of more than 2.5 g, preferably more than 10 g and yet more preferably more than 16 g of isotonic saline solution per gram of foam polymer. The absorption capacity is determined in accordance with DIN EN 13726-1:2002 (3 min measurement). Such a foam can absorb and reliably trap pathogens and cell debris, but nevertheless rest on the wound in a soft and supple manner and with a good cushioning effect while doing so.

Preferably, the hydrophilic polyurethane foam has a mean pore size of less than 1000 μm, especially 100 to 1000 μm, preferably 100 to 500 μm and very particularly preferably 100 to 300 μm. The preferred method for determining pore size is the measurement of the diameter of a multiplicity of pores on a sectional plane oriented in parallel to the wound contact side of the foam layer or of the wound care product. Pore size can be measured by viewing the pores in a light or electron microscope and comparing the pore diameter with an appropriate standard. The foam can have a homogeneous pore size or a pore-size gradient across the thickness of the foam layer. When using a foam having a pore-size gradient, an efficient discharge of wound exudate is ensured by a pore-size reduction starting from the wound contact layer, from larger pores on the wound contact side (mean pore size of, for example, 200-300 μm) right up to smaller pores on the foam side facing away from the wound during use (mean pore size of, for example, 100-200 μm). An efficient discharge of wound exudate arises because it is possible to generate a capillary effect for a particularly good absorption of liquids. At the same time, the foam can provide a sufficient amount of moisture for a wound. A foam having a pore-size gradient across the thickness of the foam and a pore size of less than 1000 μm is, for example, used in the product Permafoam from Paul Hartmann AG. Furthermore, it is particularly advantageous when the wound dressing also comprises a water vapor-permeable polyurethane cover layer. Furthermore, it is advantageous when the vapor-permeable polyurethane cover layer exhibits a water-vapor permeability ("upright", measured in accordance with DIN EN 13726-2 at a temperature of 37° C.) of more than 600 g/m² in 24 h.

Furthermore, it is conceivable and advantageous when the wound dressing comprises a mesh-shaped hydrogel on the wound side. Furthermore, it is advantageous when the wound dressing comprises a polyurethane cover layer on the side distant from the wound.

Furthermore, it is advantageous when the foam has a density of 70 to 110 kg/m3. According to a further embodiment of the invention, it is possible to use a hydrophobic PU foam having a density of 10 to 50 kg/m3. Such foams are used especially in wound dressings intended for negative-pressure wound therapy. In a further embodiment of the invention, it would be further conceivable and advantageous to use silicone foams having a density of up to 300 kg/m3.

Polyurethane foams are usually obtainable by reacting a curable mixture comprising the components polyisocyanate and isocyanate-reactive compounds, especially polyol, and also catalysts, blowing agents and optionally additives. The isocyanates used can be generally known aliphatic, cycloaliphatic and/or especially aromatic polyisocyanates. Suitable for preparing the polyurethanes are, for example, diphenylmethane diisocyanate, here in particular 4,4'-diphenylmethane diisocyanate, mixtures of monomeric diphenylmethane diisocyanates and higher polycyclic homologs of the diphenylmethane diisocyanate, tetramethylene diisocyanate, hexamethylene diisocyanate, toluene diisocyanate or mixtures thereof. The isocyanate-reactive compounds used are usually polyols such as polyetherols and/or polyesterols.

What have become apparent as particularly advantageous embodiments are, furthermore, foam wound dressings comprising a polyurethane foam, the layer thickness of which comprises 0.1 cm to 1.8 cm, preferably from 0.3 cm to 1.5 cm and very particularly preferably from 0.5 cm to 1.0 cm. The layer thickness can be the same at every point of the wound contact layer or assume different values in different regions of the wound contact layer. In particular, the absorbent layer or the polyurethane foam also comprises flattened edges.

Preferably, the wound care product has a substantially quadratic basic shape. In this connection, particular preference is given to a size range of from 8 cm×8 cm up to 20 cm×20 cm. The thickness of the wound care product is preferably less than 2 cm, the foam layer preferably having a thickness between 0.1 cm and 1.8 cm.

According to the present invention, the wound contact layer used can be an additional material. Here, a wound contact layer is in direct contact with the wound when using the wound dressing according to the invention. The wound contact layer can only and solely serve to space the foam from the wound to be treated. The additional layer has the advantage of ensuring, in the case of a dressing change, a detachment of the wound care product that is particularly gentle to tissue. The wound contact layer can exercise further functions with regard to the wound to be treated. For example, the wound contact layer can provide the wound with moisture, exhibit care properties for the wound edge, reduce skin irritations or act in an antiadherent manner.

A wound dressing according to the invention can comprise a wound contact layer, with the wound contact layer comprising a hydrogel, a polymer film, a hydrocolloid matrix, a polymer mesh, a nonwoven and/or an adhesive. In the context of the invention, the term hydrogel or gel refers to a finely dispersed system composed of at least one solid phase and one liquid phase. Said solid phase forms a spongy, three-dimensional network, the pores of which are filled by a liquid (lyogel) or else a gas (xerogel). There is complete interpenetration of both phases.

Thus, in connection with the present invention, a hydrophilic polymer foam having a proportion of water of at least 10% by weight or a hydrophilic polyurethane foam having a proportion of water of at least 10% by weight is to be understood to mean such a polymer foam or polyurethane foam comprising at least 10% by weight of water, with the polymer foam or the polyurethane foam being able to release the water. In contrast, it is not to be understood to mean the proportion of water that is possibly used for the formation, for example in the polymerization of the starting products, of the polymer foam or of the polyurethane foam. This water is covalently bonded and is not available for wound treatment. Furthermore, it is neither to be understood to mean a proportion of water that is used in the preparation of the foam for production reasons. This proportion of water is withdrawn from the polymer foam after or during the formation of the foam, usually by drying, for example by drying in an oven, and is thus not available for wound treatment either. Thus, a wound dressing according to the invention comprises a polymer foam or a polyurethane foam comprising a proportion of water that distinctly exceeds above any residual water content due to the preparation process after drying.

Further preferably, a wound dressing according to the invention comprises a hydrophilic polyurethane foam having a retention value R of at least 20%. Here, the hydrophilic polyurethane foam further preferably has a retention value R of at least 30%, especially of at least 40%, especially at least 40% and very particularly preferably of at least 50%. Irrespective thereof, the wound dressing can further preferably comprise a hydrophilic polyurethane foam having a retention value R of not more than 90%, especially of not more than 80% and very particularly of not more than 70%. The retention value R is, in this connection, determined according to a method described herein.

Very particularly preferably, a wound dressing according to the invention comprises a hydrophilic polyurethane foam comprising a proportion of water of at least 10% by weight, the proportion of water corresponding to the retention value R of the polyurethane foam.

The hydrogel can be used in different ways for wound treatment. The gel can be first applied to the wound and then covered with a wound dressing. Another possibility of using the gel for wound treatment is to use a wound dressing which holds the hydrogel ready in a wound contact layer. In this way, the gel properties, which stabilize the pH within the acidic range, are provided in the wound.

What have become apparent as particularly advantageous embodiments are, furthermore, wound dressings comprising a hydrogel matrix, the layer thickness of which comprises 0.1 to 5.0 mm. In particular, a wound dressing according to the invention thus comprises a wound contact layer having a layer thickness of from 0.1 to 5.0 mm, especially from 0.5 to 5.0 mm and very particularly preferably from 0.5 to 3.0 mm. Wound dressings having such layer thicknesses exhibit, firstly, no wound adhesion and, secondly, the ability to take up a wound exudate released by a wound and to forward it to the absorbent layer. These layer thicknesses can be the same at every point of the wound contact layer or assume different values in different regions of the wound contact layer.

Further preferably, the hydrogel matrix can comprise channels, especially conical channels, for the passage of liquids from the first side to the second side. This can provide in particular an improved passage for wound exudate. Here, the channels particularly preferably have an elliptical or a circular cross section, i.e., the channels have a circular or elliptical opening both on the first side and on the second side of the hydrogel matrix, with the circular or elliptical opening on the first side and the second side being different in size. However, it is also possible for the channels to have a triangular, rectangular, square, pentagonal, hexagonal or some other polygonal cross section. In this connection, the first side very particularly preferably has openings which is larger in comparison with the opening situated on the second side.

According to a further development of the invention, the wound contact layer or the hydrogel matrix can also comprise openings having a diameter of 0.5 to 5 mm. In particular, the wound contact layer or the hydrogel matrix comprises openings having a diameter of 1 to 3 mm. Very particularly preferably, the wound contact layer or the hydrogel matrix comprises, on the first side facing the wound, openings having a diameter of 1 to 3 mm, with the second side of the wound contact layer or of the hydrogel matrix being in direct contact with the polyurethane foam.

However, a transition layer can also be arranged between the absorbent layer and the wound contact layer. In this embodiment, a wound dressing according to the invention comprises, between the hydrogel matrix and polyurethane foam, a layer comprising both materials. Said transition layer can, just like the wound contact layer, comprise channels, openings or holes. If the transition layer comprises channels, openings or holes, said channels, openings or holes are, according to a further preferred embodiment, filled with polyurethane foam. Further preferably, said channels, openings or holes are congruent to the channels, openings or holes of the wound contact layer. The arrangement of such a transition layer makes it possible to provide a wound dressing comprising a laminate composed of a polyurethane foam and a hydrogel matrix, which laminate has a particularly firm cohesion between the absorbent layer and the wound contact layer.

The hydrogels according to the invention are suitable for the treatment of wounds. The present invention therefore also encompasses hydrogels according to the invention for the treatment of wounds. In particular, the present invention encompasses hydrogels for the treatment of chronic wounds such as decubitus ulcer, pressure ulcers, pressure sore, ulcus cruris venosum, venous ulcers, ulcus cruris arteriosum, arterial ulcers, wounds as a consequence of diabetic foot, neuropathic ulcers, but also wounds as a consequence of autoimmune diseases or of tumors (ulcerating tumors) or of radiation damage in the case of tumor therapy.

Hydrogels according to the invention, or wound dressings containing them, are suitable for phase-appropriate wound therapy, especially for the therapy of wounds in the granulation phase and/or the epithelialization phase.

DESCRIPTION OF THE FIGURES

FIG. 1 shows a first wound dressing (10) according to the invention with a view of the wound contact layer. The wound dressing (10) is manufactured as a so-called island dressing and consists of a support layer (11) composed of a water-impermeable and water vapor-permeable polyurethane film coated with an acrylic adhesive (12) over its entire surface. By means of the acrylic adhesive (12), what is applied in the center of the support layer is an absorbent hydrophilic polyurethane foam layer (not depicted here), to which a hydrogel (15) according to the invention is applied as wound contact layer. The hydrophilic polyurethane foam layer comprises a proportion of water of 40% by weight of water. Thus, 100 g of a polyurethane foam used in this example comprise 40 g of water and 60 g of polyurethane matrix. The hydrogel wound contact layer (15) is connected adhesively to the absorbent polyurethane foam layer (not depicted here). Introduced into the hydrogel wound contact layer are a multiplicity of circular holes (16) to allow the flow of wound exudate from the wound into the absorbent layer. The hydrogel wound contact layer prevents an inward growth of newly formed cells into the pores of the polyurethane foam.

FIG. 2 shows a further embodiment of a wound dressing according to the invention. The wound dressing (20) comprises a support layer (21) congruent with an absorbent layer (23) and composed of a water-impermeable and water vapor-permeable polyurethane foam, which support layer (21) is connected to the absorbent layer (23) by means of a discontinuous adhesive layer (22) composed of an acrylic adhesive. The discontinuous application means that regions (27) of the absorbent layer and of the support layer remain unconnected. The wound dressing comprises an absorbent layer (23) having a layer thickness of 4 mm and a support layer (21) having a layer thickness of 1.5 mm. The absorbent layer (23) is formed from an open-pore hydrophilic polyurethane foam having a pore size of on average 220 μm. The polyurethane foam comprises, at the same time, a proportion of water of 70% by weight. Applied to the first side of the polyurethane foam is a hydrogel according to the invention as wound contact layer (25). With a basis weight of 75 g/m$^2$, the hydrogel is not applied continuously on the polyurethane foam, with the result that circular holes (26) are provided in the hydrogel wound contact layer (25) for the improved passage of wound exudate. The polyurethane foam comprises a first side having an area of 25 cm$^2$, with the holes (26) occupying altogether an area of 5 cm$^2$.

FIG. 3 shows a third embodiment of a wound dressing according to the invention. The wound dressing (30) comprises a support layer (31) composed of a water-impermeable and water vapor-permeable polyurethane film, an absorbent layer (33) composed of an open-pore hydrophilic polyurethane foam having a proportion of water of 52.8% by weight (based on the polyurethane foam) and a wound contact layer (35) composed of a hydrogel according to the invention having a proportion of water of approx. 57.9% by weight (based on the hydrogel). The entire surface of the support layer (31) is laminated onto the hydrophilic polymer foam by means of an acrylic adhesive (32) applied to the polymer film. An aqueous hydrogel (35) according to the invention, comprising a polyurethane-polyurea copolymer, is applied on the first side of the absorbent layer that faces the wound during use. The hydrogel wound contact layer is provided with conical channels (36) which are circular in cross section (in parallel to the wound), with the result that an improved flow of wound exudate from the wound into the absorbent hydrophilic foam can occur (cf. FIG. 3a). When preparing the wound dressing, the still viscous hydrogel has slightly penetrated into the polyurethane foam, and what is formed between the hydrogel wound contact layer and the hydrophilic polyurethane foam is therefore a transition layer (34) consisting of the hydrogel and the hydrophilic polyurethane foam. The transition layer on its part comprises channels (37) which are filled only with polyurethane foam and which are arranged congruently to the channels in the hydrogel wound contact layer.

FIG. 4 shows a fourth embodiment of a wound dressing according to the invention. The wound dressing (40) comprises a support layer (41) composed of a water-impermeable and water vapor-permeable polyurethane film, a layer (42) composed of aqueous hydrogel according to the invention, and a two-part cover layer (43) composed of siliconized paper. The hydrogel layer has a thickness of 3 mm.

EXAMPLES

Examples 1-13

Preparation of the Gels

Figure 1:
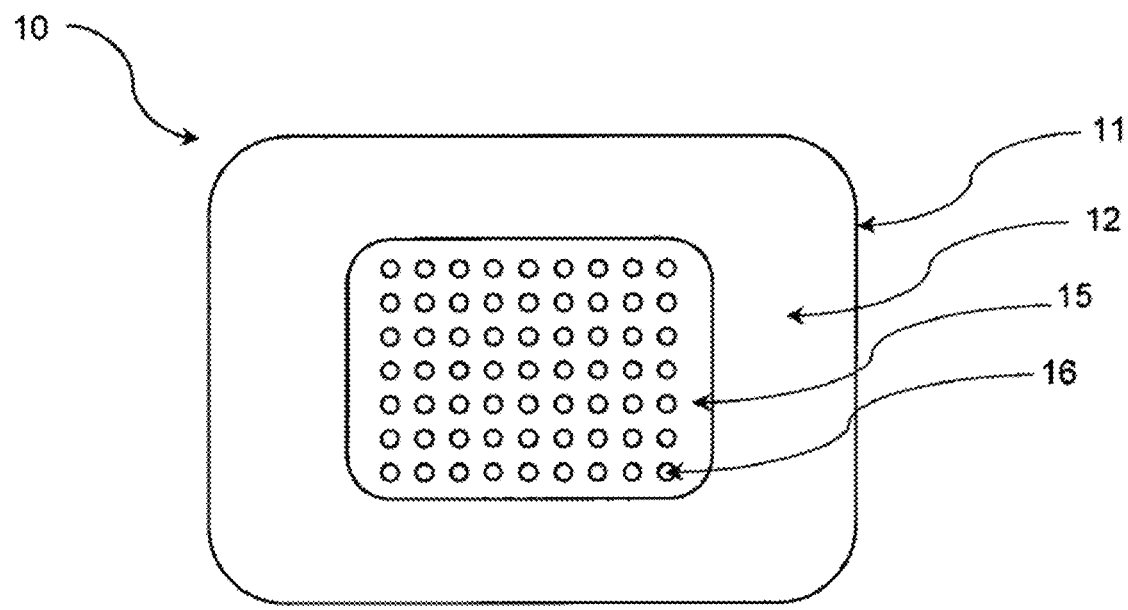
FIG. 1: A first wound dressing according to the invention
Figure 2:
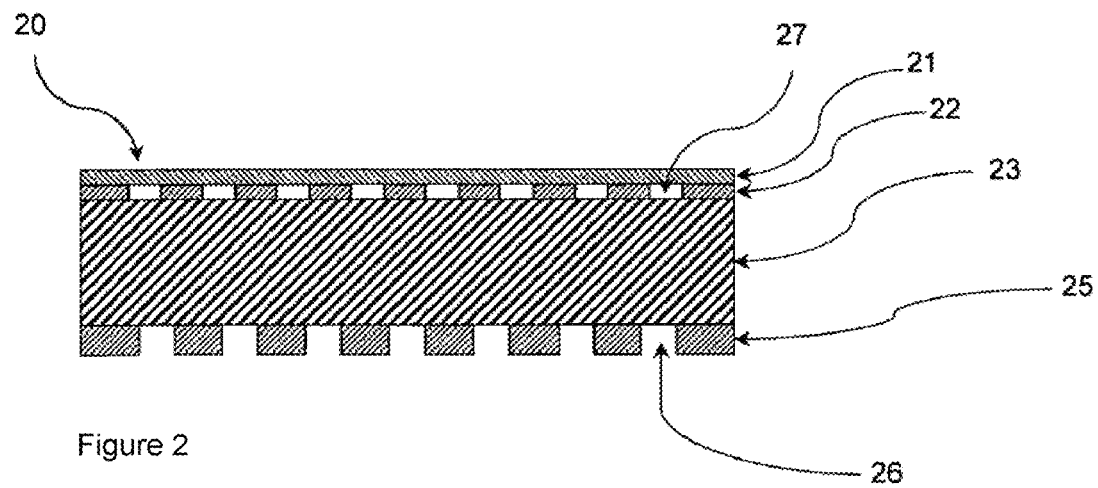
FIG. 2: A second wound dressing according to the invention in cross section
Figures 3, 3A:
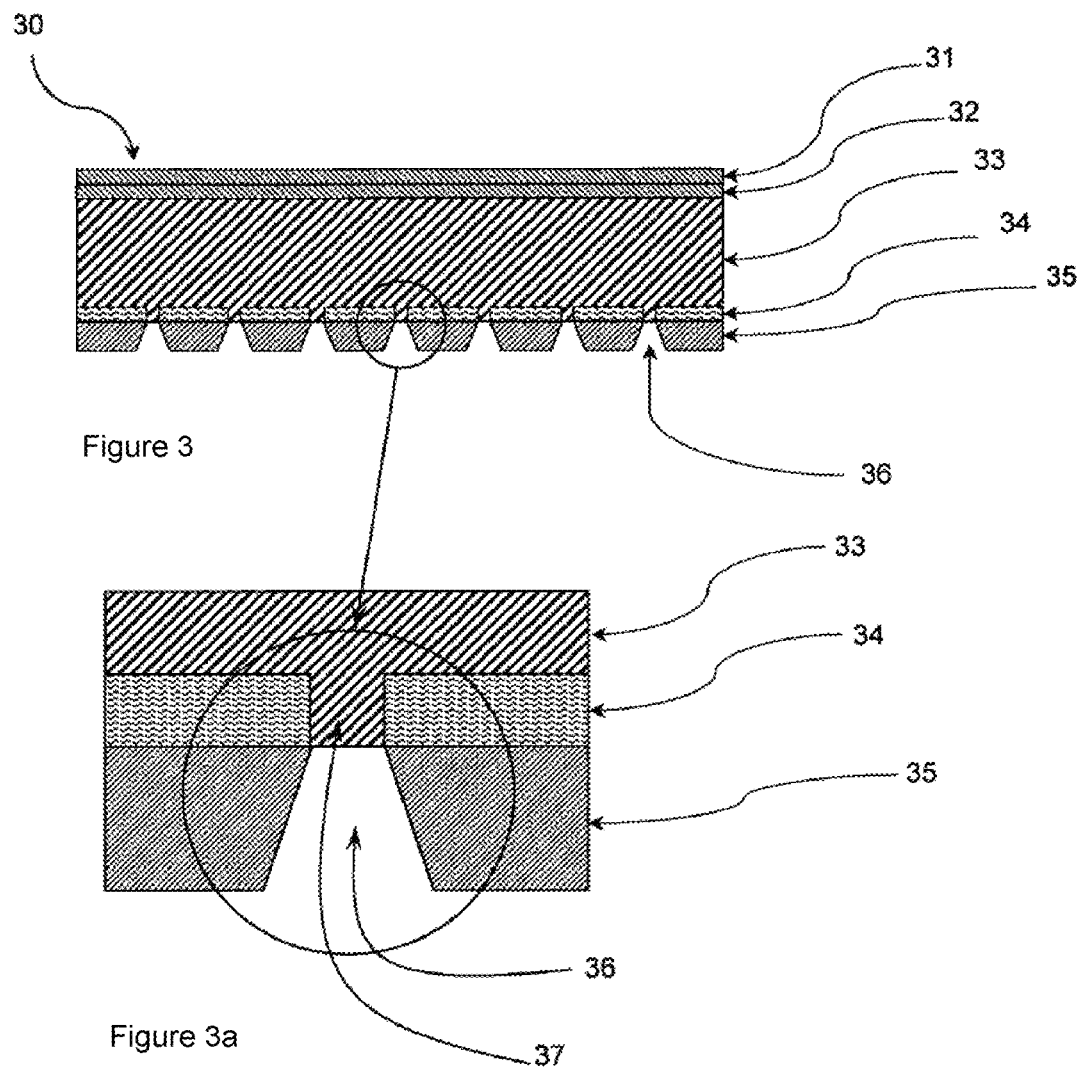
FIG. 3: A third wound dressing according to the invention in cross section
FIG. 3a: A subsection of the third wound dressing according to the invention in cross section
Figure 4:
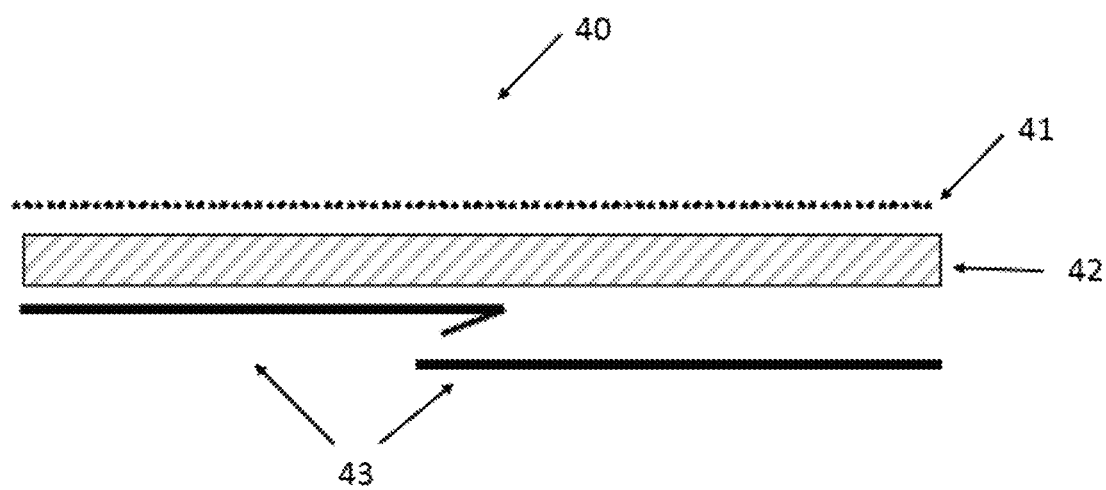
FIG. 4: A fourth wound dressing according to the invention in cross section

Mixtures of alcohol, demineralized water and sodium chloride are prepared according to Table 1 below.

TABLE 1

Mixtures of alcohol, water and sodium chloride

| Example No. | Designation of gel | Alcohol | Demin. water | NaCl |
|---|---|---|---|---|
| 1 | Glycerol 5% | 70.4 g of glycerol | 916.0 g | 13.6 g |
| 2 | Glycerol 10% | 140.8 g of glycerol | 845.6 g | 13.6 g |
| 3 | Glycerol 15% | 211.3 g of glycerol | 775.1 g | 13.6 g |
| 4 | Glycerol 20% | 281.7 g of glycerol | 704.7 g | 13.6 g |
| 5 | Glycerol 25% | 352.1 g of glycerol | 634.3 g | 13.6 g |
| 6 | Glycerol 30% | 422.5 g of glycerol | 563.9 g | 13.6 g |
| 7 | Ethylene glycol 20% | 281.7 g of ethylene glycol | 704.7 g | 13.6 g |
| 8 | Sorbitol 20% | 281.7 g of sorbitol | 704.7 g | 13.6 g |
| 9 | Sucrose 20% | 281.7 g of sucrose | 704.7 g | 13.6 g |
| 10 | PEG300 20% | 281.7 g of PEG 300 | 704.7 g | 13.6 g |
| 11 | PEG2000 20% | 281.7 g of PEG 2000 | 704.7 g | 13.6 g |
| 12 | $H_2O$ | — | 986.4 g | 13.6 g |
| 13 | Propylene glycol | 281.7 g of propylene glycol | 704.7 g | 13.6 g |

In a second step, 3.465 g of Jeffamin are melted at 50° C. and mixed with 3.135 g of demineralized water. This amount of Jeffamin contains 3.31 mmol of reactive amine end groups. The mixture obtained is mixed with 28.4 g of an alcohol mixture prepared according to the table and 5.0 g of Aquapol with vigorous stirring and ice-cold water cooling. This amount of Aquapol contains 3.84 mmol of reactive isocyanate end groups. In this connection, the molar ratio of reactive isocyanate end groups to reactive amine groups is in each case 1.16. The mixture obtained is poured out and is spread out to form a gel having a thickness of 3 mm.

The masses of the constituents used in the reaction to prepare the gels have the proportions indicated in Table 2, based on the total mass of the reactants used:

TABLE 2

Proportions by mass of the reactants used

| Example No. | Jeffamin ED-2003 | Aquapol PL-13000-3 | Alcohol | Demin. Wasser | NaCl |
|---|---|---|---|---|---|
| 1 | 8.7% | 12.5% | 5.0% | 72.9% | 1.0% |
| 2 | 8.7% | 12.5% | 10.0% | 67.9% | 1.0% |
| 3 | 8.7% | 12.5% | 15.0% | 62.9% | 1.0% |
| 4 | 8.7% | 12.5% | 20.0% | 57.9% | 1.0% |
| 5 | 8.7% | 12.5% | 25.0% | 52.9% | 1.0% |
| 6 | 8.7% | 12.5% | 30.0% | 47.9% | 1.0% |
| 7 | 8.7% | 12.5% | 20.0% | 57.9% | 1.0% |
| 8 | 8.7% | 12.5% | 20.0% | 57.9% | 1.0% |
| 9 | 8.7% | 12.5% | 20.0% | 57.9% | 1.0% |

TABLE 2-continued

Proportions by mass of the reactants used

| Example No. | Jeffamin ED-2003 | Aquapol PL-13000-3 | Alcohol | Demin. Wasser | NaCl |
|---|---|---|---|---|---|
| 10 | 8.7% | 12.5% | 20.0% | 57.9% | 1.0% |
| 11 | 8.7% | 12.5% | 20.0% | 57.9% | 1.0% |
| 12 | 8.7% | 12.5% | 0.0% | 77.9% | 1.0% |
| 13 | 8.7% | 12.5% | 20.0% | 57.9% | 1.0% |

Example No. 12 is a comparative example without polyhydric alcohol.

Example No. 13 is a comparative example according to WO2010/000451.

Example 14

Measurement of Moisture Loss

Moisture loss describes the loss of weight over a certain period at a defined temperature.

Moisture loss is calculated according to the following equation and is specified in the unit g/g:

$$\text{Moisture loss} = \frac{\text{Final weight}}{\text{Starting weight}}$$

For the gels of the exemplary embodiments, the moisture losses indicated in Table 3 were ascertained:

TABLE 3

Moisture loss in g/g gel

| Example No. | Sample | Moisture loss [g/g] | | | | |
|---|---|---|---|---|---|---|
| | | 2 h | 4 h | 6 h | 8 h | 24 h |
| 1 | Glycerol 5% | 0.857 | 0.763 | 0.716 | 0.682 | 0.583 |
| 2 | Glycerol 10% | 0.861 | 0.779 | 0.724 | 0.702 | 0.641 |
| 3 | Glycerol 15% | 0.865 | 0.791 | 0.747 | 0.734 | 0.726 |
| 4 | Glycerol 20% | 0.884 | 0.827 | 0.785 | 0.756 | 0.688 |
| 5 | Glycerol 25% | 0.927 | 0.874 | 0.840 | 0.824 | 0.802 |
| 6 | Glycerol 30% | 0.951 | 0.914 | 0.894 | 0.883 | 0.864 |
| 7 | Ethylene glycol 20% | 0.943 | 0.910 | 0.887 | 0.874 | 0.819 |
| 8 | Sorbitol 20% | 0.804 | 0.698 | 0.637 | 0.596 | 0.510 |
| 9 | Sucrose 20% | 0.795 | 0.672 | 0.631 | 0.611 | 0.582 |
| 10 | PEG300 20% | 0.828 | 0.708 | 0.663 | 0.646 | 0.638 |
| 11 | PEG2000 % | 0.806 | 0.710 | 0.645 | 0.604 | 0.516 |
| 12 | H2O | 0.781 | 0.641 | 0.560 | 0.505 | 0.299 |
| 13 | Propylene glycol 20% | 0.832 | 0.720 | 0.655 | 0.617 | 0.529 |

Example 15

Measurement of Absorption Capacity

To measure absorption capacity, gel samples having a diameter Ø of 5 cm are punched out. Thereafter, they are placed in a beaker containing V=300 ml of deionized water. Subsequently, they are reweighed at certain intervals. Absorption capacity is calculated according to the following equation and is specified in the unit g/g:

$$\text{Absorption capacity} = \frac{\text{Final weight} - \text{Starting}}{\text{Starting weight}}$$

For the gels of the exemplary embodiments, the absorption capacities indicated in Table 4 were ascertained:

TABLE 4

Absorption capacity in g/g gel

| Example No. | Sample | Absorption capacity [g/g] | | | | |
|---|---|---|---|---|---|---|
| | | 2 h | 4 h | 6 h | 8 h | 24 h |
| 1 | Glycerol 5% | 1.195 | 1.574 | 1.844 | 2.027 | 2.511 |
| 2 | Glycerol 10% | 1.209 | 1.581 | 1.859 | 2.061 | 2.707 |
| 3 | Glycerol 15% | 1.635 | 2.237 | 2.654 | 3.043 | 3.894 |
| 4 | Glycerol 20% | 1.647 | 2.171 | 2.514 | 2.815 | 3.706 |
| 5 | Glycerol 25% | 1.743 | 2.337 | 2.806 | 3.096 | 4.111 |
| 6 | Glycerol 30% | 1.845 | 2.463 | 2.855 | 3.157 | 4.183 |
| 7 | Ethylene glycol 20% | 2.200 | 3.026 | 3.663 | 3.945 | 5.331 |
| 8 | Sorbitol 20% | 1.997 | 2.734 | 3.377 | 3.965 | 5.994 |
| 9 | Sucrose 20% | 2.704 | 3.498 | 4.124 | 4.587 | 5.877 |
| 10 | PEG300 20% | 2.759 | 3.641 | 4.245 | 4.785 | 6.820 |
| 11 | PEG2000 20% | 1.527 | 2.276 | 2.597 | 2.819 | 3.044 |
| 12 | H2O | 1.230 | 1.703 | 2.022 | 2.141 | 2.670 |
| 13 | Propylene glycol 20% | 1.694 | 2.313 | 2.655 | 2.958 | 3.836 |

Example 16

Measurement of Adhesive Force

The term adhesive force describes the ability of an adhesive to adhere to a surface. It corresponds to the force required to detach a body which has come into contact with the gel surface from said surface, and is ascertained with the aid of a Zwick 010 static materials testing machine. The tests are carried out at a standard temperature of T=23° C. and a relative humidity of 50% rh. The gels must be conditioned under the test conditions for 24 hours before the test. For each measurement, three samples, each having a size of 5 cm×5 cm, are punched out from the gels in each case. The samples are affixed on a horizontally movable slide, via the side which faces away from the wound, with a double-sided adhesive tape. The approach speed of the slide is 100 mm/min, the contact time with the gel surface is 2 s and the withdrawal speed of the slide is 400 mm/min. The test body (weight=0.245 N) moves downward until it comes into contact with the surface of the gel, where it resides for a period of t=2 s. After this contact time, the test body moves upward and measures the force required for the detachment of the body from the gel surface.

Example 17

Test for Cell Compatibility

The tests for cell compatibility were carried out in accordance with DIN EN ISO 10993-5 and the procedural instructions from the *Abteilung für Funktionswerkstoffe der Medizin and der Zahnheilkunde* [department of functional materials in medicine and dentistry]: BioLab 973302, 042901, 964702 and 964805, and comprise measurements of cell growth, metabolic activity and protein content.

The hydrogels were delivered in a sterile state in Petri dishes. For the test, what were weighed out were, in each case, 0.1 g/ml culture medium of the samples.

For each sample, cellular activity, cell count and protein concentration were each tested in quadruplicate three times. The elution time was 48 h, and the incubation of the cells with the eluates was also 48 h.

The cell line used was L 929 CC1 mouse fibroblasts, American Type Culture Collection, Rockville, Md., USA.

The culture medium used for preliminary culture and elution was DMEM (Dulbecco's Mod. Eagle Medium) according to procedural instructions BioLab 042901.

The negative control used was polystyrene from Nunc GmbH & Co KG, Wiesbaden. The positive control used was Vekoplan KT PVC plates from Konig GmbH, Wendelstein.

For each sample, three eluates, each from one hydrogel, which were prepared on different test days were tested. To this end, the hydrogels in the Petri dishes were halved in the middle using a sterile scalpel and transferred into a sterile 50 ml reaction vessel. For each 0.1 g of sample, 1 ml of elution medium was added to the hydrogels and this was then eluted for 48 h at 37° C. and 5% CO2 in an incubator. To remove any suspended solids from the eluates, the samples were centrifuged for 5 min at 4000 rpm after the incubation and filtered through a filter (pore size 0.2 μm).

The cells were seeded at a concentration of 50 000 cells/ml, and the preliminary culture was carried out at 37° C. and 5% CO2 for 24 h. Thereafter, the DMEM medium added in the seeding was removed and the cells were each covered with 1 ml of eluate at a concentration of 100%. As negative control, DMEM medium was incubated for 48 h in a 50 ml Falcon tube like the samples and, as positive control, what was used was the eluate of the plastic disks at a concentration of 100%. After incubation for 48 hours, cellular activity, cell count and total protein content were determined.

Cell Growth

After enzymatic detachment of the cells using Accutase, the cells were counted with the aid of a cell counter.

Viability Test via Metabolic Activity

Viability is tested using tetrazolium salt, WST 1, Roche Diagnostics GmbH Mannheim, according to the information from the manufacturer. WST 1 is converted by succinate dehydrogenase (citric acid cycle enzyme) in the mitochondria of the metabolically active cells to form the colored formazan and is measured photometrically. The absorption values (OD), determined at 450 nm and 620 nm, correlate with the respiratory activity of the cultured cells.

Protein Content

Protein content is tested using the DC Protein Assay, BIO-RAD GmbH Munich, according to the information from the manufacturer. Lowry protein determination is based on the reduction of Cu(II) to form Cu(I) by the aromatic tyrosine/tryptophan residues of proteins. In a further step, the copper-protein complex reduces a phosphomolybdic acid/phosphotungstate reagent to form molybdenum and tungsten blue. The absorbance of this intense blue color is measured photometrically at 750 nm. By running a standard series at the same time, it is possible to determine the protein concentration.

Acceptance and Evaluation

The classification of the score ranges for acceptance and evaluation was done in accordance with DIN EN ISO 7405 and the term inhibitory dose (ID 50: dose at which 50% of cells are inhibited in terms of growth) (literature: *Allgemeine Pharmakologie and Toxikologie* [general pharmacology and toxicology], Henschler, editor: Forth Wolfgang; Spektrum akad. Verl. Heidelberg; 7th edition 1996). Severe growth inhibition, moderate inhibition and slight inhibition are characterized by a cell growth of 0-29%, a cell growth of 30-59% and a cell growth of 60-79%, respectively, in comparison with the control. Cell growth rates between 80% and 100% indicate noninhibited cell growth.

Severely reduced metabolic activity, moderately reduced metabolic activity and slightly reduced metabolic activity are characterized by a cellular activity of 0-29%, a cellular activity of 30-59% and a cellular activity of 60-79%, respectively, in comparison with the control. Cellular activity rates between 80% and 100% indicate a nonreduced metabolic activity.

Severe reduced protein content and moderately reduced protein content are characterized by a protein concentration of 0-34% and a protein concentration of 35-69%, respectively, in comparison with the control. Protein concentrations between 70% and 100% indicate a nonreduced protein content.

For the gels of the exemplary embodiments, the cell compatibilities indicated in Table 5 were ascertained:

TABLE 5

Cell compatibility

| Example No. | Sample | Inhibition of cell growth | Reduction of metabolic activity | Reduction of protein content |
|---|---|---|---|---|
| 1 | Glycerol 5% | Slight | Moderate | Moderate |
| 2 | Glycerol 10% | Slight | Slight | None |
| 3 | Glycerol 15% | Slight | Slight | None |
| 4 | Glycerol 20% | Slight | Slight | None |
| 5 | Glycerol 25% | Slight | Slight | None |
| 6 | Glycerol 30% | Moderate | Slight | None |
| 7 | Ethylene glycol 20% | Moderate | Moderate | Moderate |
| 8 | Sorbitol 20% | Moderate | Severe | Moderate |
| 9 | Sucrose 20% | Slight | Moderate | None |
| 10 | PEG300 20% | Severe | Severe | Moderate |
| 11 | PEG2000 20% | Moderate | Moderate | Moderate |
| 12 | H2O | Slight | Slight | Moderate |
| 13 | Propylene glycol 20% | Severe | Severe | Moderate |

The invention claimed is:

1. A wound dressing comprising a backing layer and a layer comprising an aqueous hydrogel for the treatment of wounds obtainable by reacting an a) amine-terminated prepolymer containing polyalkylene oxide units with an b) isocyanate-terminated prepolymer containing polyalkylene oxide units, the reaction taking place in the presence of a polyhydric alcohol, except propylene glycol, and in the presence of water and, based on the total mass of all reactants,
the sum total of the masses of amine-terminated prepolymer and isocyanate-terminated prepolymer being 10-30% by weight of the total mass of all reactants and
the mass of the polyhydric alcohol, except propylene glycol, being 5-35% by weight of the total mass of all reactants and
the mass of the water used being at least 40% by weight of the total mass of all reactants, and
the molar ratio of reactive isocyanate end groups to reactive amine end groups being 1.0 to 2.0.

2. The wound dressing of claim 1, wherein the polyhydric alcohol is glycerol.

3. The wound dressing of claim 2, wherein the glycerol is used in an amount of 15-25% by weight.

4. The wound dressing of claim 1 wherein the layer comprising the aqueous hydrogel is a wound contact layer.

5. The wound dressing of claim 4, wherein the wound dressing further comprises one or more distributor layers.

6. The wound dressing of claim 1, wherein the hydrogel is obtainable by reacting an a) amine-terminated prepolymer containing polyethylene oxide units and/or polypropylene oxide units with an b) at least three-armedly branched isocyanate-terminated prepolymer containing polyethylene oxide units and/or polypropylene oxide units.

7. The wound dressing of claim 1, wherein the polyalkylene oxide units in (a) and (b) are both polyethylene oxide and polypropylene oxide units in a weight ratio of polyethylene oxide units to polypropylene oxide units of from 3:1 to 7:1.

8. The The wound dressing aqueous hydrogel of claim 1, wherein the polyhydric alcohol is selected from the group consisting of ethylene glycol, glycerol, sorbitol, PEG300, PEG2000 and sucrose.

9. The wound dressing of claim 1, wherein the polyhydric alcohol is used in a proportion of 10-25% by weight, based on the total mass of all reactants.

10. The wound dressing of claim 1, wherein the glycerol is used in an amount of 10-25% by weight.

11. The wound dressing of claim 1, wherein the reaction further takes place in the presence of 0.5-1.5% by weight of a salt selected from the group consisting of sodium chloride, potassium chloride, magnesium chloride, calcium chloride and combinations thereof.

12. The wound dressing of claim 1, wherein the wound dressing additionally comprises an absorbent layer which is arranged between the backing layer and the layer comprising the aqueous hydrogel.

13. The wound dressing of claim 1, wherein the layer comprising an aqueous hydrogel is continuous.

14. The wound dressing of claim 1, wherein the layer comprising an aqueous hydrogel comprises holes, openings or channels.

15. A method of treating chronic wounds comprising applying the wound dressing of claim 1 to a chronic wound.

16. A method of concentrating would healing-promoting growth factors comprising applying the wound dressing of claim 1 to wound healing-promoting growth factors in a wound.

17. A method of treating a wound in a granulation and/or epithelialization phase comprising applying the wound dressing of claim 1 to a wound in the granulation and/or epithelialization phase.

18. The wound dressing of claim 1, wherein the molar ratio of reactive isocyanate end groups to reactive amine end groups is 1.0 to 1.5.

* * * * *